United States Patent [19]

Sabb

[11] Patent Number: 5,756,501

[45] Date of Patent: May 26, 1998

[54] SATURATED AND UNSATURATED PYRIDAZINO[4,5-B] INDOLIZINES USEFUL AS ANTIDEMENTIA AGENTS

[75] Inventor: Annmarie L. Sabb, Pennington, N.J.

[73] Assignee: American Home Products Corporation, Madison, N.J.

[21] Appl. No.: 770,383

[22] Filed: Dec. 3, 1996

Related U.S. Application Data

[60] Provisional application No. 60/008,548, Dec. 13, 1995.

[51] Int. Cl.$^6$ .................. A01N 43/58; C07D 237/26
[52] U.S. Cl. ............................. 514/248; 544/234
[58] Field of Search ..................... 544/234; 514/248

[56] References Cited

U.S. PATENT DOCUMENTS 4,985,560  1/1991  Sabb .......................... 544/115

OTHER PUBLICATIONS

Uchida, T., et al., Journal of Heterocyclic Chemistry 15, 1303 (1978).

*Primary Examiner*—Mukund J. Shah
*Assistant Examiner*—Tamthom T. Ngo
*Attorney, Agent, or Firm*—R. F. Boswell, Jr.

[57] ABSTRACT

This invention relates to novel compounds which bind to central cholinergic muscarinic M1 receptors and may be useful for treatment of diseases attributed to cholinergic insufficiency such as presenile dementia, senile dementia of the Alzheimer's type, Parkinson's disease, Down's syndrome, and dementia pugilistica. The compounds useful in this invention have the formula

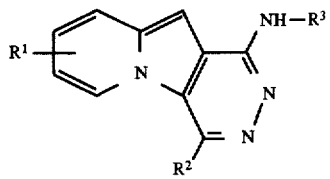

or a 6, 7, 8, 9 tetrahydro analog thereof, where $R^1$ is selected from H, $C_1$–$C_6$ alkyl, $C_3$–$C_6$ cycloalkyl, $C_1$–$C_6$ alkoxy, cyano, halo, nitro, and —$NR^4R^5$, where $R^4$ and $R^5$ are independently selected from H, $C_1$–$C_6$ alkyl and phenyl, optionally substituted with halo, cyano, hydroxy, nitro, amino, mono or di $C_1$–$C_6$ alkylamino, phenylamino, $C_1$–$C_6$ alkyl or $C_1$–$C_6$ alkoxy;

$R^2$ is $CF_3$—, $CF_3CH_2$—, or —$CH_2$—X—$R^6$ where X is oxygen or NH and $R^6$ is $C_1$–$C_6$ alkyl, phenyl-$(CH_2)_n$— or —$(CH_2)_n$—$NR^7R^8$ where $R^7$ and $R^8$ are selected from H or $C_1$–$C_6$ alkyl, or $R^2$ is equal to $R^3$, and when the compound is hydrogenated at positions 6, 7, 8, and 9, $R^2$ can also be $C_1$–$C_6$ alkyl, and $R^3$ is —$(CH_2)_m$—$NR^9R^{10}$ where $R^9$ and $R^{10}$ are independently H, $C_1$–$C_6$ alkyl, phenyl, phenyl-$(CH_2)_n$—, or $NR^9R^{10}$ forms a mono or bicyclic azacycloalkane group having from 5 to 10 members, one of which may be a heteroatom selected from O, S, or $NR^{11}$ where $R^{11}$ is $C_1$–$C_6$ alkyl, phenyl, pyrimidinyl, pyridinyl, or pyrazinyl or $R^9$ is H and $R^{10}$ is a mono or bicyclic azacycloalkyl group having from 5 to 10 members where the nitrogen is either a bridgehead nitrogen or the nitrogen may be optionally substituted with $C_1$–$C_6$ alkyl, phenyl-$(CH_2)_n$— or $C_3$–$C_6$ cycloalkyl;

n is 1–6 and m is 2–5;

or a pharmaceutically acceptable salt thereof.

21 Claims, No Drawings

SATURATED AND UNSATURATED PYRIDAZINO[4,5-B] INDOLIZINES USEFUL AS ANTIDEMENTIA AGENTS

This patent application claims priority to the United States Provisonal Application Number 60/008,548 filed on Dec. 13, 1995.

FIELD OF THE INVENTION

This invention relates to novel compounds having CNS activity. More particularly it relates to novel pyridazino[4,5-b]indolizine and 6,7,8,9-tetrahydropyridazino[4,5-b]indolizine compounds which bind to central cholinergic muscarinic receptors and, therefore, may be useful for treatment of diseases involving hypofunction of the cholinergic system. Neurological illnesses related to cholinergic deficiency include presenile dementia and senile dementia of the Alzheimer's type (SDAT), Parkinson's disease, Down's Syndrome, and dementia pugilistica. Cognitive disorders which occur with these conditions include forgetfulness, confusion, memory loss, attentional deficits, and deficits in visual perception.

BACKGROUND OF THE INVENTION

The "cholinergic hypothesis" [R. T. Bartus, R. L. Dean III, B. Beer, A. S. Lippa, Science, (Jul. 30, 1982) 217:408–417, "The Cholinergic Hypothesis of Geriatric Memory Dysfunction" suggests that memory loss due to decreased levels of acetylcholine can be ameliorated by correcting the levels of acetylcholine in the brain using an acetylcholine releasing agent, an acetylcholine esterase inhibitor, or by using a drug which mimics acetylcholine (cholinomimetic). Marketing of the acetylcholine esterase inhibitor, tacrine, has demonstrated that improvement in memory can be shown in patients with mild to moderate Alzheimer's Disease [M. Williams, Curr. Opin. Invest. Drugs (May 1993) 2(5):541–544, "Tacrine-recommendation for approval"]. The utility of this drug is limited, however, because of adverse side effects especially at the higher doses where it is most effective. Clinical studies using the natural alkaloid, arecoline, a cholinergic agonist, have also demonstrated memory improvement in patients with mild to moderate Alzheimer's Disease. Because of the short half-life of arecoline, the clinical study was done using continuous infusion of the drug over a 2 week period; In addition, a peripheral muscarinic antagonist, N-methylscopolamine, was also administered during the study to prevent potential autonomic side effects. [T. T. Soncrant, K. C. Raffaele, S. Asthana, A. Berardi, P. P. Morris, and J. V. Haxby, Psychopharmacology (1993) 112:421–427, "Memory improvement without toxicity during chronic, low dose intravenous arecoline in Alzheimer's disease"]

Cholinergic receptors which bind to and are activated by the alkaloid, muscarine, are called muscarinic receptors. Three pharmacologically defined subtypes of muscarinic receptors have been identified. They are referred to as M1, M2, and M3 based upon their affinity for the M1 antagonist, pirenzepine, the M2 antagonist, AFDX-116, and the M3 antagonist, 4-diphenylacetoxy N-methylpiperidine methiodide (4-DAMP). Five different human muscarinic receptors have been cloned. The Hm1 (human m1) receptor is found primarily in brain. [T. I. Bonner, Trends in Pharmacological Sciences, supplement, Jul. 20–27 (1989) p 11–15, "New types of muscarinic acetylcholine receptors"]. Activation of the m1 receptor results in an increase in phosphoinsoitide hydrolysis (PI turnover).[K. Fukuda, et al. , Ibid., p. 4–10, "Selective effector coupling of muscarinic acetylcholine receptor subtypes"]. Carbachol, like muscarine, is able to fully activate m1 receptors. These compounds, however, contain a quaternary ammonium group and as a result are not able to cross the blood brain barrier and enter the CNS. On the contrary, compounds of this invention do not contain a quaternary ammonium group and thus can enter the CNS. The compounds of this invention bind to M1 receptors in brain and are useful for treatment of symptoms of central cholinergic insufficiency.

U.S. Pat. No. 4,985,560 discloses a class of pyridazino [4,5-b]indolizines which bind to central cholinergic M1 receptors and are useful for treatment of diseases involving hypofunction of the cholinergic system. It has now been found that substitution in position 4 improves affinity to central M1 cholinergic receptors. Surprisingly, reduction of the pyridine ring of the pyridazino[4,5-b]indolizine compounds of this invention significantly increases M1 affinity and selectivity for M1 versus M2 receptors in brain. Examples of saturated pyridazino[4,5-b]indolizines of this invention are not covered in the above patent.

The synthesis of the tetrahydroindolizine ring by means of a 1,3-dipolar cycloaddition reaction has been reported as has its conversion to a tetrahydropyridazino[4,5-b]indolizine ring. The latter resulted from the reaction of hydrazine with adjacent benzoyl substituents on the tetrahydroindolizine ring.[Uchida, T., et al., J. Heterocyclic Chem. 15, 1303 (1978)]

SUMMARY OF THE INVENTION

The compounds of the present invention are characterized by the general formula

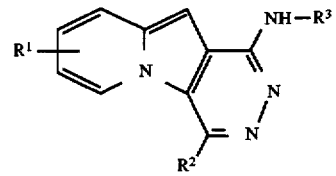

or a 6, 7, 8, 9 tetrahydro analog thereof, where $R^1$ is selected from H, $C_1$–$C_6$ alkyl, $C_3$–$C_6$ cycloalkyl, $C_1$–$C_6$ alkoxy, cyano, halo, nitro, and —$NR^4R^5$, where $R^4$ and $R^5$ are independently selected from H, $C_1$–$C_6$ alkyl and phenyl, optionally substituted with halo, cyano, hydroxy, nitro, amino, mono or di $C_1$–$C_6$ alkylamino, phenylamino, $C_1$–$C_6$ alkyl or $C_1$–$C_6$ alkoxy;

$R^2$ is $CF_3$—, $CF_3CH_2$—, or —$CH_2$—X—$R^6$ where X is oxygen or NH and $R^6$ is $C_1$–$C_6$ alkyl, phenyl-$(CH_2)_n$— or —$(CH_2)_n$—$NR^7R^8$ where $R^7$ and $R^8$ are selected from H or $C_1$–$C_6$ alkyl, or $R^2$ is equal to $R^3$, and when the compound is hydrogenated at positions 6, 7, 8, and 9, $R^2$ can also be $C_1$–$C_6$ alkyl, and $R^3$ is —$(CH_2)_m$—$NR^9R^{10}$ where $R^9$ and $R^{10}$ are independently H, $C_1$–$C_6$ alkyl, phenyl, phenyl-$(CH_2)_n$—, or $NR^9R^{10}$ forms a mono or bicyclic azacycloalkane group having from 5 to 10 members, one of which may be a heteroatom selected from O, S, or $NR^{11}$ where $R^{11}$ is $C_1$–$C_6$ alkyl, phenyl, pyrimidinyl, pyridinyl, or pyrazinyl or $R^9$ is H and $R^{10}$ is a mono or bicyclic azacycloalkyl group having from 5 to 10 members where the nitrogen is either a bridgehead nitrogen or the nitrogen may be optionally substituted with $C_1$–$C_6$ alkyl, phenyl-$(CH_2)_n$— or $C_3$–$C_6$ cycloalkyl;

n is 1–6 and m is 2–5;

or a pharmaceutically acceptable salt thereof.

In the above definitions of terms, the term $C_1$–$C_6$ alkyl includes straight and branched chain hydrocarbons such as methyl, ethyl, propyl, isopropyl, butyl, t-butyl and the like. A pharmaceutically acceptable salt is an acid addition salt formed by an invention compound and a pharmaceutically acceptable inorganic or organic acid such as hydrochloric acid, sulfuric acid, phosphoric acid, acetic acid, formic acid, fumaric acid, citric acid, maleic acid, or methanesulfonic acid.

The preferred compounds of this invention are those of Examples 1–15.

DETAILED DESCRIPTION OF THE INVENTION

Compounds of this invention may be prepared by a variety of synthetic routes using conventional methods or commercially available starting materials (Scheme I).

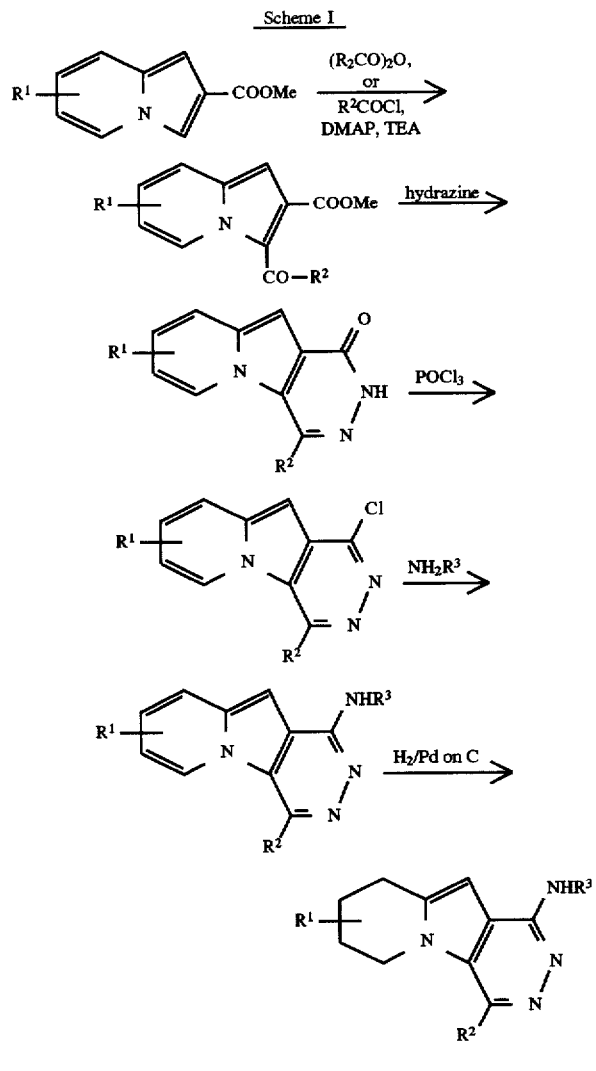

Thus a substituted or unsubstituted 2-indolizinecarboxylic acid ester is treated with an acylating agent, such as an acid anhydride or acid chloride in the presence of a base such as triethylamine [TEA], and an acylation catalyst such as N,N-dimethylaminopyridine [DMAP], to give a substituted or unsubstituted 3-acyl-2-indolizinecarboxylic acid ester. The acyl ester is then allowed to react with hydrazine hydrate in a polar solvent, such as ethanol, to give a 4-substituted-pyridazino[4,5-b]indolizin-1-one. Treatment of the pyridazino[4,5-b]indolizin-1-one with a chlorinating agent, such as phosphorus oxychloride, gives a 1-chloro-4-substituted-pyridazino[4,5-b]indolizine. The 1-chloropyridazino[4,5-b]indolizine is allowed to react with a di or triamine compound at elevated temperatures to give an unsubstituted or substituted 1-(di or triamino)-4-substituted-pyridazino[4,5-b]indolizine of the present invention. Catalytic hydrogenation of these pyridazino[4,5-b]indolizines using a catalyst, such as palladium on carbon, in a hydrogenation apparatus, such as a Parr apparatus, in an acidic polar mixture, such as acetic acid and methanol with or without addition of a stronger acid, such as sulfuric acid, gives the 6,7,8,9-tetrahydropyridazino[4,5-b]indolizines of this invention.

An alternate route to compounds of this invention involves catalytic reduction of the pyridine ring of 4-substituted-pyridazino[4,5-b]indolizin-1-ones using hydrogen and a catalyst, such as palladium on carbon, under pressure in an apparatus, such as a Parr apparatus, in an acidic polar solvent mixture, such as a mixture of water, acetic acid and ethanol containing sulfuric acid (Scheme II). The 6,7,8,9-tetrahydropyridazino[4,5,-b]indolizin-1-ones are then treated with a chlorinating agent, such as phosphorus oxychloride to give 1-chloro-4-substituted-6,7,8,9-tetrahydropyridazino[4,5-b]indolizines. Reaction of these chloro compounds with di or triamines at elevated temperatures gives substituted or unsubstituted 1-(di or triamino)-4-substituted-6,7,8,9-tetrahydropyridazino[4,5-b]indolizines of the present invention.

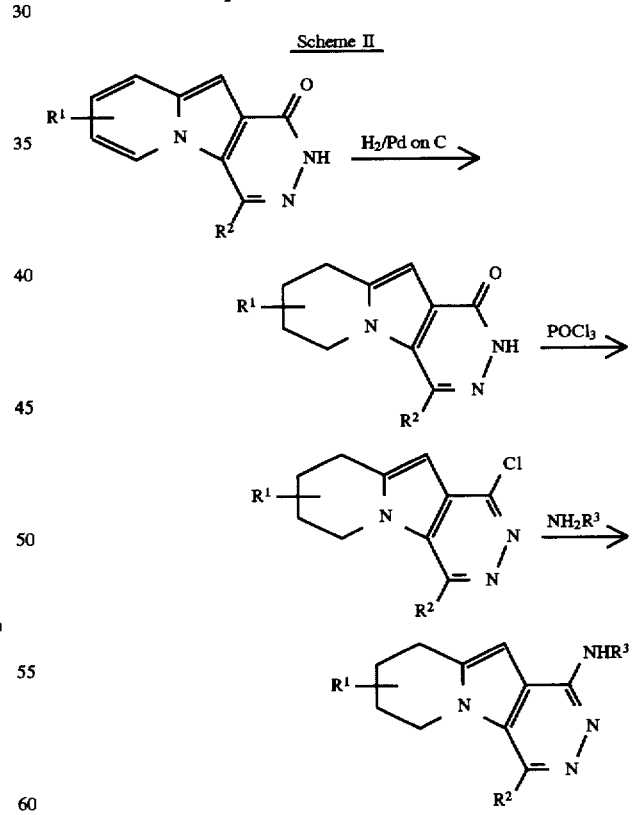

Treatment of intermediates of this invention, 4-hydroxymethyl-pyridazino[4,5-b]indolizin-1-ones, with a chlorinating agent, such as phosphorus oxychloride, gives 1-chloro-4-chloromethylpyridazino[4,5,-b]indolizines. Reaction of these dichloro compounds with di or triamines gives compounds of this invention (Scheme III).

Scheme III

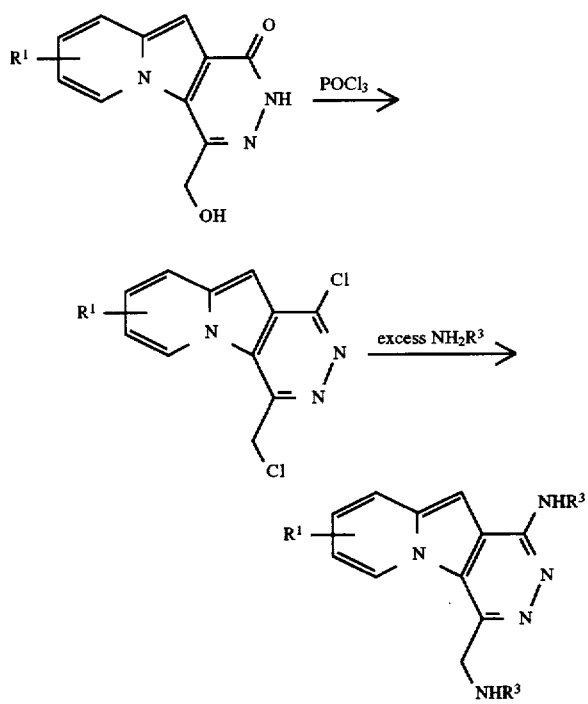

2-Indolizinecarboxylic acid which may be variously substituted as desired [Bragg et al., J. Chem. Soc., 3277 (1963)] is converted to an ester (methanol treated with an acid such as HCl) to give the intermediate 2-carbomethoxyindolizine used in the following procedures.

Alternatively, the indolizine-2-carboxylates used in Scheme I can be prepared from appropriately substituted 2-methylpyridines that are either commercially available, such as 5-butyl-2-methyl pyridine, 6chloro-2-picoline, 2-amino-6-methyl pyridine, 2-cyano-6-methyl pyridine or 2,4-dimethylpyridine, or may be prepared according to standard literature synthetic procedures. 5-Methylindolizine-2-carboxylic acid is disclosed by Bode et al., *J. Chem. Soc., Perk. Trans.* 1, 3023–3027 (1994) and references therein. 5-Cyanoindolizine-2-carboxylic acid methyl ester is disclosed by Abramovitch and Mathur in *Heterocycles* 5(1), 91–94 (1976) and the 6-ethoxy and methoxy analogs of indolizine-2-carboxylic acid are disclosed by De and Saha in *J. Pharm. Sci.* 64(2), 249–252 (1975). The synthetic route to the indolizine-2-carboxylates from a 2-methylpyridine is shown in scheme IV.

Scheme IV

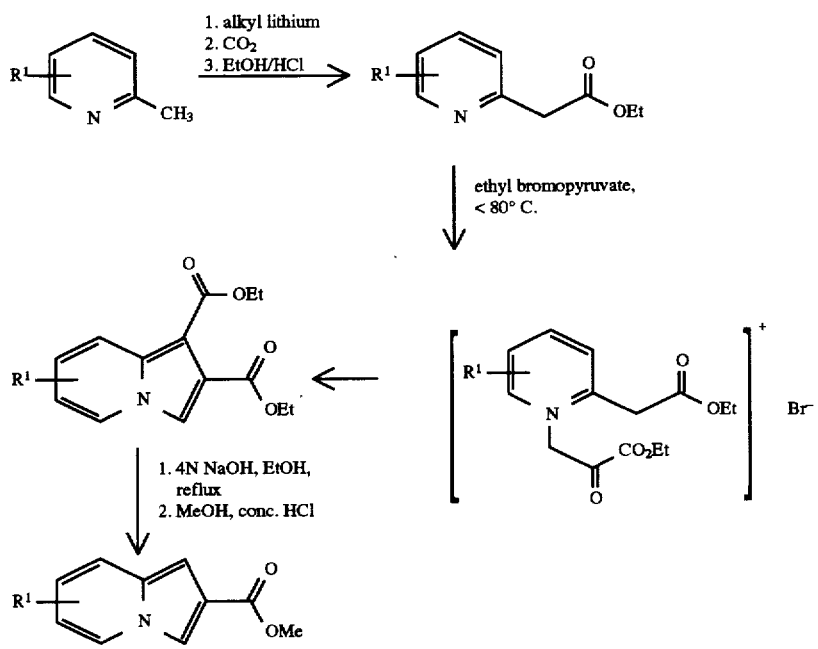

7

The following specific examples are included for illustrative purposes and should not be construed as limiting this disclosure in any way. Invention compounds can be prepared by a person skilled in the art using chemicals and intermediates that are either commerically available or prepared according to literature procedures.

EXAMPLE 1

N-[4-(3-Azabicyclo[3.2.2]non-3-yl)butyl]-4-(trifluoromethyl)pyridazino[4,5b]indolizine-1-amine 2-Carbomethoxyindolizine (3.00 g, 17.14 mmol) was dissolved in methylene chloride containing N,N-dimethylaminopyridine (DMAP, 0.230 g, 1.89 mmol) and triethylamine (TEA, 2.08 g, 20.57 mmol). Trifluoroacetic anhydride (3.96 g, 18.86 mmol) was added slowly (addition time: 45 minutes) and the reaction mixture was allowed to heat under reflux for 72 hours. The organic phase was washed with water and then passed through a pad of silica gel eluting the product with 20% hexane in methylene chloride. 3-Trifluoroacetyl-2-carbomethoxyindolizine (I) (3.95 g) was obtained in 85% yield as a yellow-green oil.

A mixture of (I) (3.60 g, 13.3 mmol) and excess 85% aqueous hydrazine in ethanol (250 mL) was heated under reflux for 10 minutes (a precipitate formed). After cooling in a freezer overnight, the solid was collected by filtration and dried to give 4-trifluoromethylpyridazino[4,5-b]indolizin-1-one (II, 2.65 g, 79%)

Compound II (2.62 g, 10.3 mmol) and phosphorus oxychloride (3.18 mL, 34 mmoL) were combined and heated under reflux for 2 days. After cooling to room temperature, the reaction mixture was poured into ice water and made basic with aqueous sodium hydroxide (pH>7). The product was collected by filtration and dried in a vacuum oven overnight to give 2.82 g (100%) of 1-chloro-4-trifluoromethylpyridazino[4,5-b]indolizine (III)

A mixture of chloro compound III (620 mg, 2.28 mmol) and 4-(3-azabicyclo[3.2.2]nonyl)butylamine (896 mg, 4.57 mmol), 123 mg of ammonium chloride and 0.4 mL of triethylamine was heated under reflux for 2 days. After cooling, the reaction mixture was dissolved in methylene chloride and the organic phase was washed three times with water. The organic phase was dried over magnesium sulfate, evaporated under reduced pressure and purified by flash column chromatography on silica gel eluting with 40:60 methanol:ethyl acetate. The title compound (561 mg, 57%) was converted to the hydrochloride salt using ethereal HCl and ether: m.p. 245°–246° C.

Anal. Calc'd for $C_{23}H_{28}F_3N_5 \cdot 2$ HCl $\cdot 1.75$ H$_2$O: C, 50.41; H, 6.36; N, 12.48
Found: C, 50.27; H, 6.42; N, 12.75

EXAMPLE 2

N-[3-(3-Azabicyclo[3.2.2]non-3-yl)propyl-4-(trifluoromethyl)pyridazino[4,5-b]indolizine-1-amine According to the procedure of Example 1, chloro compound III was allowed to react with 3-(3-azabicyclo[3.2.2]non-3-yl)propylamine to give the title compound which was converted to the hydrochloride salt, m.p.252°–253° C.
Anal. Calcd for $C_{22}H_{26}F_3N_5 \cdot 2$ HCl$\cdot 1.75$ H$_2$O: C, 50.63 H, 6.08; N, 13.42
Found: C, 50.85; H, 6.48; N, 13.26.

EXAMPLE 3

N,N-Diethyl-N'-[4-(methoxymethyl)pyridazino[4,5-b]indolizin-1-yl]-1,3-propanediamine 2-Carbomethoxyindolizine (15.0 g, 85.6 mmol) was dissolved in dichloroethane containing N,N-dimethylaminopyridine (DMAP, 1.15 g, 9.45mmol) and triethylamine (TEA, 10.40 g, 103 mmol). Methoxyacetyl chloride (9.44 g, 87 mmol) was added and the reaction mixture was allowed to heat under reflux in a nitrogen atmosphere for 72 hours. The organic phase was washed with water, aqueous sodium hydroxide, and dilute HCl. The organic phase was dried (M$_g$SO$_4$) and evaporated to give a residue which was purified by high pressure liquid chromatography (silica gel, methanol in methylene chloride ) to give 2-carbomethoxy-3-methoxymethylacetylindolizine IV (7.06 g, 33%).

A mixture of (IV) [7.06 g, 30.5 mmol] and excess 85% hydrazine hydrate in ethanol (300 mL) was heated under reflux (a precipitate formed). After cooling, the solid was collected by filtration and dried to give 4-methoxymethylpyridazino[4,5-b]indolizin-1-one (V, 6.81 g, 97%)

Compound V (6.3 g, 27.5 mmol) and phosphorus oxychloride (100 mL) were combined and heated under reflux for 4 hours. Most of the POCl$_3$ was removed using a rotary evaporator. The residue was poured into ice water and the aqueous phase was extracted with methylene chloride using a continuous extractor apparatus. Evaporation of the solvent gave a residue which was purified by flash chromatography on silica gel eluting with 3:7 isopropanol:methylene chloride to give the chloro compound, VI (6.8 g, 81%).

A mixture of chloro compound VI (0.98 g, 3.95 mmol), 4 equivalents of N'-diethylaminopropylamine (2.04 g, 15.8 mmol) , and 1 equivalent of triethylamine (0.61 mL) was heated in N-methylpyrrolidinone at 120° C. overnight. After cooling, the reaction mixture was dissolved in methylene chloride and the organic phase was washed three times with water. The organic phase was dried over magnesium sulfate, evaporated under reduced pressure and purified by flash column chromatography on silica gel eluting with 93:5:2 methylene chloride:methanol:triethylamine. The title compound (1.14 g mg, 85%) was converted to the hydrated dihydrochloride salt using ethereal HCl and ether: m.p. 111°–112° C.
Anal. Calcd for $C_{19}H_{27}N_5O \cdot 2$ HCl$\cdot 2$ H$_2$O: C, 50.67; H, 7.38; N, 15.47
Found: C, 50.82; H, 7.24; N, 15.08

EXAMPLE 4

N-[3-(3-Azabicyclo[3.2.2]non-3-yl)propyl]-4-(methoxymethyl)pyridazino[4,5-b]indolizin-1-amine Following the procedure of Example 3, chloro compound VI (0.50 g, 2.02 mmoL) was allowed to react with 3-(3-azabicyclo[3.2.2]non-3-yl)propylamine (0.911 g, 5 mmoL) in N-methylpyrrolidinone containing TEA. The crude product was purified by flash column chromatography on silica gel eluting with 10–15% methanol in methylene chloride containing 1% ammonium hydroxide. The title compound was converted to the hydrated dihydrochloride salt, m.p. 229°–232° C.
Anal. Calcd for $C_{23}H_{31}N_5O \cdot 2$ HCl$\cdot 1/2$ H$_2$O$\cdot 1/4$ CHCl$_3$: C, 55.26; H, 6.83; N, 13.86
Found: C, 55.04; H, 6.76; N, 13.51

EXAMPLE 5

N-[4-(3-Azabicyclo[3.2.2]non-3-yl)butyl]-4-(methoxymethyl)pyridazino[4,5-b]indolizin-1-amine Following the procedure of Example 3, chloro compound VI (1.00 g, 4.04 mmoL) was allowed to react with 4-(3- azabicyclo[3.2.2]non-3-yl)butylamine (2.21 g 12.12 mmoL) in N-methylpyrrolidinone containing TEA and ammonium chloride (1 equiv). The crude product was purified by flash column chromatography on silica gel eluting with 10–15% methanol in methylene chloride containing 1% ammonium hydroxide. The title compound was converted to the hydrated dihydrochloride salt, m.p. 220° C. (dec.).

Anal. Calc'd for $C_{24}H_{33}N_5O \cdot 2$ HCl$\cdot 0.75$ $H_2O$: C, 57.83; H,7.48; N, 14.05

Found: C, 58.35; H,7.45; N, 14.18.

EXAMPLE 6

4-[(Phenylmethoxy)methyl]-N-[2-[4-(2-pyrimidinyl)-1-piperazinyl]ethyl]pyridazino[4,5-b]indolizin-1-amine Following the procedure of Example 3, 2-carbomethoxyindolizine was reacted with benzyloxyacetyl chloride to give 3-benzyloxyacetyl-2-carbomethoxyindolizine (VII) Cyclization of VII with hydrazine and reaction of the resulting pyridazino[4,5-b] indolizin-1-one with POCl$_3$ gave the corresponding chloro compound (VIII). The reaction of VII with 4-(2-pyrimidinyl)-1-piperizinyl)ethyl amine gave the title compound. Treatment with ethereal HCl in ether gave the product as the trihydrochloride salt: m.p. 140° C.

Anal. Calc'd for $C_{28}H_{30}N_8O \cdot 3HCl \cdot 0.75$ $H_2O$: C, 54.46; H,5.63; N, 18.15

Found: C, 54.24; H,5.81; N, 18.36.

EXAMPLE 7

N,N-Diethyl-N'-[4-[[[3-(diethylamino)propyl]amino] methyl]-pyridazino[4,5-b]indolizin-1-yl]-1,3-propanediamine Following the procedure of Example 3, reaction of 2-carbomethoxyindolizine with acetoxyacetyl chloride gave 3-acetyloxyacetyl-2-carbomethoxyindolizine (IX). Reaction of IX with 1.5 equiv of anhydrous hydrazine in dry ethanol gave 4-hydroxymethylpyridazino[4,5-b]indolizin-1-one which upon refluxing with excess POCl$_3$ gave 1-chloro-4-chloromethylpyridazino[4,5-b]indolizine (X). Compound X (1.0 g, 4.0 mmol) was combined with excess N,N-diethylaminopropylamine (2.68 mL, 17 mmoL) in N-methylpyrrolidinone (2 mL) containing TEA (0.74 mL, 1.2 equiv.) and 1.2 equiv. of ammonium chloride (vigorous initial reaction with gas evolution). When the reaction subsided the stirred reaction mixture was heated at 100° C. overnight. After cooling to room temperature, the volatiles were removed by vacuum distillation. The residue was dissolved in methylene chloride and extracted with water (3 times), dried (MgSO$_4$), and the solvent evaporated. The residue was purified by flash column chromatography on silica gel eluting with 20% methanol in methylene chloride containg 2% ammonium hydroxide. The isolated free base was converted to the tetra hydrochloride salt using ethereal HCl in ether m.p. 120°–123° C.

Anal. Calcd for $C_{25}H_{41}N_7 \cdot 4$ HCl$\cdot 1.5$ $H_2O$: C, 49.02; H,7.90; N, 16.00

Found: C, 49.15; H,7.95; N, 15.89.

EXAMPLE 8

N,N-Diethyl-N'-[6,7,8,9-tetrahydro-4-(methyl)-pyridazino[4,5-b]indolizin-1-yl]-1,3-propanediamine 4-(Methyl)-N,N-diethyl-N'-[pyridazino[4,5-b]indolizin-1-yl]-1,3-propanediamine (2.75 g, 8.83 mmoL) was hydrogenated in a Parr appartus with 10% Pd on charcoal (0.54 g) in a 1:1 mixture of acetic acid and methanol at 55 psi and room temperature. Filtration through Solka Floc to remove the catalyst and evaporation of the filtrate gave a crude product which was passed through a pad of alumina eluting with 5% methanol in methylene chloride to give the free base of the title product in quantitative yield. The free base was converted to the monofumarate salt: m.p.171°–172° C.

Anal. Calc'd for $C_{18}H_{29}N_5 \cdot C_4H_4O_4 \cdot 0.5$ $H_2O$: C, 59.98 H,7.78; N,15.90

Found: C, 59.99; H.7.93; N,15.76.

EXAMPLE 9

N-[2-(3-Azabicyclo[3.2.2non-3-yl)ethyl]-6,7,8,9-tetrahydro-4-(methyl)pyridazino[4,5-b]indolizin-1-amine 4-Methylpyridazino[4,5-b]indolizin-1-one (5.08 g, 25.5 mmol) was hydrogenated at room temperature and 55 psi using a Parr apparatus in a mixture containing 100 mL each of water, ethanol and acetic acid, 3 mL of concentrated sulfuric acid, and 10% Pd on charcoal (500 mg). A white precipitate was observed. The precipitate and catalyst were filtered through Solka Floc and the solids were washed with methanol and methylene chloride. The washes were evaporated to give 6,7,8,9-tetrahydro-4-(methyl)pyridazino[4,5-b] indolizin-1-one (XI). The reduction filtrate was evaporated in vacuo to remove most of the volatiles, then filtered to isolate additional XI. The aqueous phase was then washed with methylene chloride to extract the remaining XI. The product from all three fractions was combined and dried in vacuo to give 3.2 g (67%) of XI.

Compound XI (3.00 g, 15 mmol) was heated under reflux with excess POCl$_3$ (25 mL) until no starting material remained (TLC, silic gel, 5% methanol in methylene chloride), then poured over ice, made basic with aqueous sodium hydroxide and the aqueous phase extracted with methylene chloride to isolate the product. The organic phase was dried (MgSO$_4$), filtered, and evaporated to give a residue which was purified by flash column chromatography (silica gel, 5% methanol in methylene chloride) to give 1-chloro-4-methyl-6,7,8,9-tetrahydropyridazino[4,5-b] indolizine XII (3.00 g, 92%)

A mixture of compound XII (0.51 g, 2.31 mmoL), 2-(3-azabicyclo[3.2.2]non-3-yl)ethylamine 0.970 g, 2.5 equiv.) , ammonium chloride (1 equiv.) and N-methylpyrrolidinone were heated under reflux in a nitrogen atmosphere overnight. No starting material remained by TLC (silica gel, 20% methanol in methylene chloride). The reaction mixture was diluted with methylene chloride and washed successively with sat. sodium bicarbonate and water. The organic phase was dried (MgSO$_4$), filtered, evaporated and the residue purified by flash column chromatography on silica gel eluting with methanol in methylene chloride containing a gradient of ammonium hydroxide. The title compound (0.52 g, 67%) was recovered and converted to the dihydrochloride salt: m.p. 272°–274° C.

Anal. Calc'd for $C_{21}H_{31}N_5 \cdot 2$ HCl$\cdot 0.5$ $H_2O$: C, 57.93; H, 7.87; N, 16.08

Found: C, 58.30; H, 7.86; N, 16.02

EXAMPLE 10

N-[3-(3-Azabicyclo[3.2.2]non-3-yl)propyl]-6,7,8,9-tetrahydro-4-(methyl)pyridazino[4,5-b]indolizin-1-amine Following the procedure in Example 9, compound XII was allowed to react with 3-(3-azabicyclo[3.2.2]non-3-yl)

propylamine to give the title compound which was converted to the dihydrochloride salt: m.p.278°–279° C.
Anal. Calcd for $C_{22}H_{33}N_5 \cdot 2$ HCl$\cdot 2H_2O$: C, 55.46; H, 8.25; N, 14.70
Found: C, 55.27; H, 8.31; N, 14.46.

EXAMPLE 11

N-[4-(3-Azabicyclo[3.2.2]non-3-yl)butyl]-6,7,8,9-tetrahydro-4-methylpyridazino[4,5-b]indolizin-1-amine Following the procedure in Example 9, compound XII was allowed to react with 4-(3-azabicyclo[3.2.2]non-3-yl)butylamine to give the title compound which was converted to the dihydrochloride salt: m.p.210° C. (dec.).
Anal. Calc'd for $C_{23}H_{35}N_5 \cdot 2$ HCl$\cdot 2H_2O$: C, 56.32; H, 8.43; N, 14.28
Found: C, 56.28; H, 8.35; N, 14.28.

EXAMPLE 12

N-[4-(3-Azabicyclo[3.2.2]non-3-yl)butyl]-6,7,8,9-tetrahydro-4-(trifluoromethyl)-pyridazino[4,5-b]indolizin-1-amine The title compound of Example 1 (360 mg, 0.72 mmol), 10% Pd on charcoal (72 mg), ethanol and acetic acid (about 50 mL each), and 1.5 mL of concentrated sulfuric acid were hydrogenated at 55 psi in a Parr apparatus overnight. The reaction mixture was filtered through a pad of Solkafloc and the filtrate was evaporated under reduced pressure. The residue was dissolved in water and the aqueous solution was adjusted to pH 7 with aqueous sodium hydroxide and then extracted several times with methylene chloride. The organic phase was dried and the solvent removed under reduced pressure to give the title compound. Treatment of the title compound with ethereal HCl in ether gave the hydrated dihydrochloride salt as a tan solid: m.p.140° C.
Anal. Calc'd for $C_{23}H_{32}F_3N_5 \cdot 2$ HCl$\cdot 1$ $H_2O$: C, 52.47; H, 6.89; N, 13.30
Found: C, 52.49; H, 7.16; N, 13.59.

EXAMPLE 13

N,N-Diethyl-N'-[6,7,8,9-tetrahydro-4-(methoxymethyl)-pyridazino[4,5-b]indolizin-1-yl]-1,3-propanediamine Following the procedure in Example 12, the compound in Example 3 was converted to the title compound. The product was treated with ethereal HCL in ether to obtain the hydrated dihydrochloride salt as a yellow solid: m.p.145°–147° C.
Anal. Calc'd for $C_{19}H_{31}N_5O \cdot 2$ HCl$\cdot H_2O$: C, 52.29; H, 8.08; N, 16.04
Found: C, 52.45; H, 7.99; N, 15.59.

EXAMPLE 14

N-[4-(3-Azabicyclo[3.2.2]non-3-yl)butyl]-6,7,8,9-tetrahydro-4-(methoxymethyl)-pyridazino[4,5-b]indolizin-1-amine Following the procedure in Example 12, the compound in Example 5 was converted to the title compound. The product was treated with ethereal HCl in ether to obtain the hydrated dihydrochloride salt as a yellow solid: m.p. 185° C. (dec.).
Anal. Calc'd for $C_{24}H_{37}N_5O \cdot 2$ HCl$\cdot H_2O \cdot 0.1 C_4H_{10}O$: C, 57.47; H, 8.30; N, 13.74
Found: C, 57.71; H, 8.23; N, 13.50.

EXAMPLE 15

6,7,8,9-Tetrahydro-N-[4-(4-morpholinyl)butyl]-4-[(phenylmethoxy)methyl]-pyradazino[4,5-b]indolizin-1-amine Following the procedure in Example 12, N-[4-(4-morpholinyl)butyl]-4-[(phenylmethoxy)methyl]-pyridazino[4,5-b]indolizin-1-amine was converted to the title compound as a light yellow solid: m.p. 144°–145° C.
Anal. Calcd for $C_{26}H_{35}N_5O_2 \cdot 2$ HCl$\cdot 2.8$ $H_2O$: C, 54.50; H, 7.49; N,12.22
Found: C, 54.43; H, 7.49; N,12.21.

Pharmacology

1. Tritiated Pirenzapine Binding Inhibition

The selective muscarinic binding by the compounds of this invention was established by determining the percentage of inhibition of [$^3$H]pirenzepine (PZ) binding to rat brain tissue at a 10 micromolar concentration. The cortex of rat brains obtained from male Sprague-Dawley rats (300 g) are homogenized using a hand-held teflon-coated pestle in 20 volumes of 0.32M sucrose. After centrifugation (747×g for 10 min at 4° C.), the resultant supernatant is decanted and recentrifuged (18677×g for 20 min at 4° C.). The resultant pellet is resuspended in the original volume of 0.32M sucrose and frozen. After thawing, the suspension is diluted (1:1 v/v) with 10 mM $Na_2HPO_4/KH_2PO_4$ buffer (pH=7.4). [$^3$H]PZ (0.5 nM, 0.04 µCi) is then incubated in multiple tubes with a 100 µl sample of the tissue suspension and 10 µl of a test compound solution (10 µM in water or ethanol) or vehicle (for control) in a sufficient quantity of the above phosphate buffer to give a total volume of 1 ml. One half of the tubes also contain 2 µM atropine sulfate which binds non-specifically with muscarinic receptors and provides for correcting the data for binding with other muscarinic receptors which may be present. After 60 minutes of incubation as 25° C. in the dark, the binding is terminated by vacuum filtration onto Whatman GF/B filters (pre-soaded for 60 minutes in 0.1% (w/v) polyethylenimine to reduce non-specific binding). After three washes with the phosphate buffer (4° C., 3 ml/wash) the vacuum is allowed to continue for two minutes before the filter-trapped radioactivity is assayed by liquid scintillation spectroscopy. Specific [$^3$H]PZ binding is defined as total binding minus binding in the presence of 2 µM atropine sulfate. Data are pesented in Table I below as the percent inhibition ([control–test]/control× 100%) of [$^3$H]PZ binding by the test or reference compound.

2. Phosphoinositide Turnover

The ability of the compounds of this invention to stimulate hydrolysis of phosphoinositide (PI) in Chinese Hampster Ovary (CHO) cells which had been transfected with CMV vector containing cDNA expressing M1 acetylcholine receptors was determined in accordance with the procedure of El-Fakahany et al., J.Pharmacol. Exp. Ther. 257, 938 (1991), whereby PI hydroxysis is performed in reaction tubes, each containing 880 µL Kreb's Buffer, 10 µL of 1.0M LiCl solution, 10 µl of the compound representative of this invention or control vehicle, and 100 µL of CHO cell suspension in Kerb's Buffer (1,000,000 cells per mL). The tubs are incubated for one hour at 37° C. The reaction is quenched with chloroform. Phase separation is assured with the addition of methanol and water followed by centrifugation. The tritiated inositol phosphates are recovered on BioRad AG 1-X8 anion exchange resin in the formate cycle. After washing the resin with water and myo-inositol, the inositol phosphates are eluted with ammonium formate/ formic acid, collected and subjected to liquid scintillation spectroscopy. The results are expressed as a percentage of the mean value obtained for carbachol ($EC_{50}$=8.0 μM).

Table I summarizes the results of the above in-vitro procedures.

TABLE I

IN VITRO PHARMACOLOGY

| COMPOUND | M1 Binding % Inhib. of [$^3$H] Pz @ 10 μM | PI Turnover % above baseline |
|---|---|---|
| Example 3 | 98.4 | |
| Example 4 | 100.5 | |
| Example 5 | 100.5 | |
| Example 6 | 98.3 | |
| Example 7 | 99.3 | |
| Example 8 | 98 | |
| Example 11 | 101 @ 1 μM | 102.5 |
| Example 13 | 109 | |
| Example 14 | 101 | 73 |
| Example 15 | 100 | |
| carbachol | | 100 |

Current evidence indicates the presence of $M_1$ and $M_2$ muscrinic receptors in the central nervous system. M2 receptors are presynaptic and function on cholinergic terminals as "autoreceptors" to modulate the release of acetylcholine. Activation of the M2 receptors inhibits acetylcholine release and is not a therapeutically desirable result for the treatment of a disease characterized by cholinergic hypofunction. M1 receptors are localized on the postsynaptic nerve cell. While the central nervous system contains a high proportin of M1 receptors, muscarinic receptors in the periphery are mainly of the M2 type. For these reasons, pharmacotherapy designed to directly enhance central cholinergic function should be targeted toward the M1 receptor, rather than the M2 receptor. In order to determine the selectivity of a test compound for M1 versus M2 receptors, it is necessary to test compounds not only for their ability to affect M1 muscarinic binding, but for their ability to affect M2 muscarinic bindings as well. Triatiated quinuclidinyl benzylate ([$^3$H]QNB) binds selectively with M2 receptors.

3. M2 Binding With [$^3$H]QNB

Male Sprague-Dawley rat brain cerebellum which contain a high proportion of M2 receptors are dissected and homogenized using a hand-held teflon-coated pestle in 20 volumes of 0.32M sucrose. After centrifugation (747×g for 10 min at 4° C.), the resultant supernatant is decanted and recentrifuged (18677×g for 20 min at 4° C.). The resultant pellet is resuspended in the original volume of 0.32M sucrose and frozen. After thawing, the suspension is diluted(1:2 v/v) with 10 mM $Na_2HPO_4KH_2PO_4$ buffer (pH=7.4). [$^3$H] quinuclidinyl benzylate (0.23 nM, 0.01 μCi) is then incubated in multiple tubes with a 100 μl sample of the tissue suspension and 10 μl of a test compound solution (10 μM in water or ethanol) or vehicle (for control) in a sufficient quantity of the above phosphate buffer to give a total volume of 1 ml. The assays are done in duplicate. One half of the tubes also contain 100 μM atropine sulfate which binds non-specifically with muscarinic receptors and provides for correcting the data for binding with other muscarinic receptors which may be present. After 60 minutes of incubation as 25° C. in the dark, the binding is terminated by vacuum filtration onto Whatman GF/B filters. After three washes with the phosphate buffer (4° C., 3 ml/wash) the vacuum is allowed to continue for two minutes before the filter-trapped radioactivity is assayed by liquid scintillation spectroscopy.

Specific [$^3$H]QNB binding is defined as total binding minus binding in the presence of 100 μM atropine sulfate. Comparison of the effects of test compounds on M2 binding with effects of M1 binding (above) will indicate the relative in vitro selectivity of test compounds toward M1 versus M2 receptors. Table II shows the selectivity of the compound of Example 11 for binding to muscarinic M1 receptors as compared to binding to muscarinic M2 receptors.

TABLE II

| COMPOUND | M1 Binding | M2 Binding | M2/M1 Ki ratio |
|---|---|---|---|
| Example 11 | Ki = 1.34 nM | Ki = 13.35 nM | 10 |

4. M1 Binding With Chinese Hampster Ovary Cells

The binding affinity of the compounds of this invention at muscarinic receptor subtypes was determined by incubating triplicate samples of homogenized Chinese Hamster Ovary (CHO) cells which had been transfected with CMV vector containing cDNA expressing individual muscarinic receptor subtypes, for one hour at 37° C. with 0.23 nM radiolabeled quinuclidinyl benzilate [$^3$H]QNB, a representative compound of this invention, and a volume of 10 mM phosphate buffer to obtain a final incubation volume of 1000 μL. Vehicle and 2 μM atropine sulfate are substituted for the test solution to determine total and non-specific bindings, respectively. After incubation, the solutions are filtered and the filter paper is subjected to scintillation spectroscopy for radioactivity counting. Specific binding in the presence of the compound of this invention is expressed as a percentage of the atropine-sensifive binding. A concentration-response evaluation is obtained through non-linear regression analysis to obtain an $IC_{50}$ and/or $K_i$ value. This procedure is based on hat of Tonnaer et al., Life Sci., 40, 1981 (1987) The results obtained with several invention compounds is shown in Table III.

TABLE III

| COMPOUND | Human m1 receptors in CHO cells: Ki (nM) |
|---|---|
| Example 1 | 240 |
| Example 2 | 140 |
| Ekample 9 | 80 |
| Example 10 | 9 |
| Example 12 | 206 |

Pharmaceutical Composition

Compounds of this invention may be administered net or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active intredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickeningk agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and raachis oil). For parenteral adminstration the carrier can also be an oily ester such as ethyl oleate and isopropyl myristate. Sterile liquid carriers are used in sterile liquid form compositions for parenteral admininstration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g., as tablets or cpsules. In such form, the comosition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from cerebral acetylcholine insufficiency must be subjectively determined by the attending physician. The variables involved include the severity of the dysfunction, and the size, age, and response pattern of the patient.

What is claimed is:

1. A compound of the formula

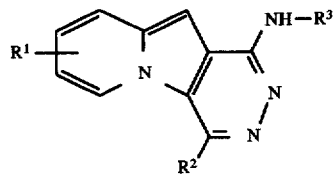

or a 6, 7, 8, 9 tetrahydro analog thereof, where $R^1$ is selected from H, $C_1$–$C_6$ alkyl, $C_3$–$C_6$ cycloalkyl, $C_1$–$C_6$ alkoxy, cyano, halo, nitro, and —$NR^4R^5$, where $R^4$ and $R^5$ are independently selected from H, $C_1$–$C_6$ alkyl and phenyl, optionally substituted with halo, cyano, hydroxy, nitro, amino, mono or di $C_1$–$C_6$ alkylamino, phenylamino, $C_1$–$C_6$ alkyl or $C_1$–$C_6$ alkoxy;

$R^2$ is $CF_3$—, $CF_3CH_2$—, or —$CH_2$—X—$R^6$ where X is oxygen or NH and $R^6$ is $C_1$–$C_6$ alkyl, phenyl-$(CH_2)_n$— or —$(CH_2)_n$—$NR^7R^8$ where $R^7$ and $R^8$ are selected from H or $C_1$–$C_6$ alkyl, or $R^2$ is equal to $R^3$, and when the compound is hydrogenated at positions 6, 7, 8, and 9, $R^2$ can also be $C_1$–$C_6$ alkyl, and $R^3$ is —$(CH_2)_m$—$NR^9R^{10}$ where $R^9$ and $R^{10}$ are independently H, $C_1$–$C_6$ alkyl, phenyl, phenyl-$(CH_2)_n$—, or $NR^9R^{10}$ forms a mono or bicyclic azacycloalkane group having from 5 to 10 members, one of which may be a heteroatom selected from O, S, or $NR^{11}$ where $R^{11}$ is $C_1$–$C_6$ alkyl, phenyl, pyrimidinyl, pyridinyl, or pyrazinyl or $R^9$ is H and $R^{10}$ is a mono or bicyclic azacycloalkyl group having from 5 to 10 members where the nitrogen is either a bridgehead nitrogen or the nitrogen may be optionally substituted with $C_1$–$C_6$ alkyl, phenyl-$(CH_2)_n$— or $C_3$–$C_6$ cycloalkyl;

n is 1–6 and m is 2–5;

or a pharmaceutically acceptable salt thereof.

2. A compound according to claim 1 which is N-[4-(3-azabicyclo[3.2.2]non-3-yl)butyl]-4-(trifluoromethyl)pyridazino[4,5-b]indolizine-1-amine or a pharmaceutically acceptable salt thereof.

3. A compound according to claim 1 which is N-[3-(3-azabicyclo[3.2.2]non-3-yl)propyl-4-(trifluoromethyl)pyridazino[4,5-b]indolizine-1-amine or a pharmaceutically acceptable salt thereof.

4. A compound according to claim 1 which is N,N-diethyl-N'-[4-(methoxymethyl)-pyridazino[4,5-b]indolizin-1-yl]-1,3-propanediamine or a pharmaceutically acceptable salt thereof.

5. A compound according to claim 1 which is N-[3-(3-azabicyclo[3.2.2]non-3-yl)propyl]-4-(methoxymethyl)pyridazino[4,5-b]indolizin-1-amine or a pharmaceutically acceptable salt thereof.

6. A compound according to claim 1 which is N-[4-(3-azabicyclo[3.2.2]non-3-yl)butyl]-4-(methoxymethyl)pyridazino[4,5-b]indolizin-1-amine or a pharmaceutically acceptable salt thereof.

7. A compound according to claim 1 which is 4-[(phenylmethoxy)methyl]-N-[2-[4-(2-pyrimidinyl)-1-piperazinyl]ethyl]pyridazino[4,5-b]indolizin-1-amine or a pharmaceutically acceptable salt thereof.

8. A compound according to claim 1 which is N,N-diethyl-N'-[4-[[[3-(diethylamino)propyl]amino]methyl]-pyridazino[4,5-b]indolizin-1-yl]-1,3-propanediamine or a pharmaceutically acceptable salt thereof.

9. A compound according to claim 1 which is N,N-diethyl-N'-[6,7,8,9-tetrahydro-4-(methyl)-pyridazino[4,5-b]indolizin-1-yl]-1,3-propanediamine or a pharmaceutically acceptable salt thereof.

10. A compound according to claim 1 which is N-[2-(3-azabicyclo[3.2.2]non-3-yl)ethyl]-6,7,8,9-tetrahydro-4-(methyl)pyridazino[4,5-b]indolizin-1-amine or a pharmaceutically acceptable salt thereof.

11. A compound according to claim 1 which is N-[3-(3-azabicyclo[3.2.2]non-3-yl)propyl]-6,7,8,9-tetrahydro-4-(methyl)pyridazino[4,5-b]indolizin-1-amine or a pharmaceutically acceptable salt thereof.

12. A compound according to claim 1 which is N-[4-(3-azabicyclo[3.2.2]non-3-yl)butyl]-6,7,8,9-tetrahydro-4-methylpyridazino[4,5-b]indolizin-1-amine or a pharmaceutically acceptable salt thereof.

13. A compound according to claim 1 which is N-[4-(3-azabicyclo[3.2.2]non-3-yl)butyl]-6,7,8,9-tetrahydro-4-(trifluoromethyl)-pyridazino[4,5-b]indolizin-1-amine or a pharmaceutically acceptable salt thereof.

14. A compound according to claim 1 which is N,N-diethyl-N'-[6,7,8,9-tetrahydro-4-(methoxymethyl)-pyridazino[4,5-b]indolizin-1-yl]-1,3-propanediamine or a pharmaceutically acceptable salt thereof.

15. A compound according to claim 1 which is N-[4-(3-azabicyclo[3.2.2]non-3-yl)butyl]-6,7,8,9-tetrahydro-4-(methoxymethyl)-pyridazino[4,5-b]indolizin-1-amine or a pharmaceutically acceptable salt thereof.

16. A compound according to claim 1 which is 6,7,8,9,-tetrahydro-N-[4-(4-morpholinyl)butyl]-4-[(phenylmethoxy)methyl]-pyridazino[4,5-b]indolizin-1-amine or a pharmaceutically acceptable salt thereof.

17. A method of alleviating the symptoms of neurological illness due to acetylcholine deficiency in a mammal which comprises administration to a mammal having such illness a therapeutically effective amount of a compound of the formula

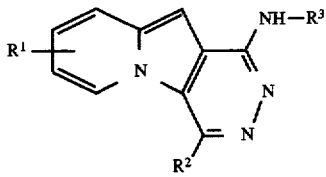

or a 6, 7, 8, 9 tetrahydro analog thereof, where $R^1$ is selected from H, $C_1$–$C_6$ alkyl, $C_3$–$C_6$ cycloalkyl, $C_1$–$C_6$ alkoxy, cyano, halo, nitro, and —$NR^4R^5$, where $R^4$ and $R^5$ are independently selected from H, $C_1$–$C_6$ alkyl and phenyl, optionally substituted with halo, cyano, hydroxy, nitro, amino, mono or di $C_1$–$C_6$ alkylamino, phenylamino, $C_1$–$C_6$ alkyl or $C_1$–$C_6$ alkoxy;

$R^2$ is $CF_3$—, $CF_3CH_2$—, or —$CH_2$—X—$R^6$ where X is oxygen or NH and $R^6$ is $C_1$–$C_6$ alkyl, phenyl-$(CH_2)_n$— or —$(CH_2)_n$—$NR^7R^8$ where $R^7$ and $R^8$ are selected from H or $C_1$–$C_6$ alkyl, or $R^2$ is equal to $R^3$, and when the compound is hydrogenated at positions 6, 7, 8, and 9, $R^2$ can also be $C_1$–$C_6$ alkyl, and $R^3$ is —$(CH_2)_m$—$NR^9R^{10}$ where $R^9$ and $R^{10}$ are independently H, $C_1$–$C_6$ alkyl, phenyl, phenyl-$(CH_2)_n$—, or $NR^9R^{10}$ forms a mono or bicyclic azacycloalkane group having from 5 to 10 members, one of which may be a heteroatom selected from O, S, or $NR^{11}$ where $R^{11}$ is $C_1$–$C_6$ alkyl, phenyl, pyrimidinyl, pyridinyl, or pyrazinyl or $R^9$ is H and $R^{10}$ is a mono or bicyclic azacycloalkyl group having from 5 to 10 members where the nitrogen is either a bridgehead nitrogen or the nitrogen may be optionally substituted with $C_1$–$C_6$ alkyl, phenyl-$(CH_2)_n$— or $C_3$–$C_6$ cycloalkyl;

n is 1–6 and m is 2–5;

or a pharmaceutically acceptable salt thereof.

18. The method according to claim 17 wherein the neurological illness being treated is presenile dementia or senile dementia of Alzheimer's type.

19. The method according to claim 17 wherein the neurological illness being treated is Parkinson's disease.

20. The method according to claim 17 wherein the neurological illness being treated is Down's syndrome.

21. A pharmaceutical composition for the alleviation of symptoms of neurological illness resulting from acetylcholine deficiency in a mammal which comprises a pharmaceutical carrier and a therapeutically effective amount of a compound of the formula

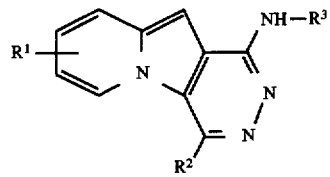

or a 6, 7, 8, 9 tetrahydro analog thereof, where $R^1$ is selected from H, $C_1$–$C_6$ alkyl, $C_3$–$C_6$ cycloalkyl, $C_1$–$C_6$ alkoxy, cyano, halo, nitro, and —$NR^4R^5$, where $R^4$ and $R^5$ are independently selected from H, $C_1$–$C_6$ alkyl and phenyl, optionally substituted with halo, cyano, hydroxy, nitro, amino, mono or di $C_1$–$C_6$ alkylamino, phenylamino, $C_1$–$C_6$ alkyl or $C_1$–$C_6$ alkoxy;

$R^2$ is $CF_3$—, $CF_3CH_2$—, or —$CH_2$—X—$R^6$ where X is oxygen or NH and $R^6$ is $C_1$–$C_6$ alkyl, phenyl-$(CH_2)_n$— or —$(CH_2)_n$—$NR^7R^8$ where $R^7$ and $R^8$ are selected from H or $C_1$–$C_6$ alkyl, or $R^2$ is equal to $R^3$, and when the compound is hydrogenated at positions 6, 7, 8, and 9, $R^2$ can also be $C_1$–$C_6$ alkyl, and $R^3$ is —$(CH_2)_m$—$NR^9R^{10}$ where $R^9$ and $R^{10}$ are independently H, $C_1$–$C_6$ alkyl, phenyl, phenyl-$(CH_2)_n$—, or $NR^9R^{10}$ forms a mono or bicyclic azacycloalkane group having from 5 to 10 members, one of which may be a heteroatom selected from O, S, or $NR^{11}$ where $R^{11}$ is $C_1$–$C_6$ alkyl, phenyl, pyrimidinyl, pyridinyl, or pyrazinyl or $R^9$ is H and $R^{10}$ is a mono or bicyclic azacycloalkyl group having from 5 to 10 members where the nitrogen is either a bridgehead nitrogen or the nitrogen may be optionally substituted with $C_1$–$C_6$ alkyl, phenyl-$(CH_2)_n$— or $C_3$–$C_6$ cycloalkyl;

n is 1–6 and m is 2–5;

or a pharmaceutically acceptable salt thereof.

* * * * *